(12) United States Patent
MacMillan et al.

(10) Patent No.: US 12,414,865 B2
(45) Date of Patent: Sep. 16, 2025

(54) IMPLANT TRIAL WITH RADIOGRAPHICALLY VISIBLE INDICIUM

(71) Applicant: CoreLink, LLC, St. Louis, MO (US)

(72) Inventors: Adam MacMillan, Quincy, MA (US); Gerhart Suppiger, St. Louis, MO (US); Brett Smith, St. Louis, MO (US)

(73) Assignee: CORELINK, LLC, St. Louis, MO (US)

( * ) Notice: Subject to any disclaimer, the term of this patent is extended or adjusted under 35 U.S.C. 154(b) by 0 days.

(21) Appl. No.: 18/732,165

(22) Filed: Jun. 3, 2024

(65) Prior Publication Data
US 2025/0073048 A1    Mar. 6, 2025

Related U.S. Application Data

(63) Continuation of application No. 17/308,725, filed on May 5, 2021, now Pat. No. 11,998,457.

(60) Provisional application No. 63/020,126, filed on May 5, 2020.

(51) Int. Cl.
*A61F 2/44* (2006.01)
*A61F 2/46* (2006.01)
*A61F 2/30* (2006.01)

(52) U.S. Cl.
CPC .......... *A61F 2/4684* (2013.01); *A61F 2/442* (2013.01); *A61F 2002/3008* (2013.01); *A61F 2002/30617* (2013.01)

(58) Field of Classification Search
CPC .......... A61F 2/4684; A61F 2/442; A61F 2/44; A61F 2/46; A61F 2002/3008; A61F 2002/30617; A61B 90/90; A61B 90/94; A61B 2017/00707

USPC .......................................... 623/17.11–17.16
See application file for complete search history.

(56) References Cited

U.S. PATENT DOCUMENTS

| | | | | |
|---|---|---|---|---|
| 6,113,639 | A * | 9/2000 | Ray | A61F 2/4684 623/17.16 |
| 6,562,041 | B1* | 5/2003 | Yonemura | A61B 17/1757 606/279 |
| 6,641,582 | B1* | 11/2003 | Hanson | A61F 2/4465 623/17.11 |
| 9,801,732 | B2* | 10/2017 | Chin | A61F 2/4455 |
| 2003/0135275 | A1* | 7/2003 | Garcia | A61B 17/1671 623/17.11 |
| 2003/0139813 | A1* | 7/2003 | Messerli | A61B 17/1671 623/17.11 |
| 2003/0233145 | A1* | 12/2003 | Landry | A61F 2/4657 606/100 |
| 2004/0019356 | A1* | 1/2004 | Fraser | A61F 2/4684 623/17.11 |
| 2004/0052333 | A1 | 3/2004 | Sayre et al. | |

(Continued)

FOREIGN PATENT DOCUMENTS

| EP | 1384455 A1 | 1/2004 |
|---|---|---|
| WO | WO2005072659 A2 | 8/2005 |
| WO | WO2014151172 A1 | 9/2014 |

*Primary Examiner* — Jessica Weiss
(74) *Attorney, Agent, or Firm* — Stinson LLP

(57) ABSTRACT

An implant trial includes a trial body and an indicium disposed in the trial body. The trial body is positionable in a subject. The indicium is designed and constructed to indicate a parameter of the implant trial. The indicium is radiographically visible when the trial body is positioned in the subject. The implant trial may be a trial spacer for vertebrae.

15 Claims, 8 Drawing Sheets

(56) References Cited

U.S. PATENT DOCUMENTS

| | | | |
|---|---|---|---|
| 2004/0059337 A1* | 3/2004 | Hanson | A61F 2/4611 606/79 |
| 2006/0129238 A1* | 6/2006 | Paltzer | A61F 2/447 606/90 |
| 2007/0093825 A1* | 4/2007 | Ferree | A61B 17/7062 623/17.11 |
| 2007/0237307 A1* | 10/2007 | Suddaby | A61B 90/39 378/205 |
| 2008/0287959 A1* | 11/2008 | Quest | A61F 2/4405 606/87 |
| 2013/0331850 A1* | 12/2013 | Bojarski | A61F 2/4657 606/102 |
| 2014/0114415 A1* | 4/2014 | Tyber | A61F 2/4455 623/17.16 |
| 2014/0243982 A1* | 8/2014 | Miller | A61F 2/447 623/17.16 |
| 2015/0223907 A1* | 8/2015 | Kieser | A61B 17/866 623/17.16 |
| 2015/0328005 A1 | 11/2015 | Padovani et al. | |
| 2015/0342757 A1* | 12/2015 | Lomeli | A61B 1/00105 623/17.16 |
| 2019/0298546 A1* | 10/2019 | Dewey | A61F 2/4684 |
| 2021/0290410 A1* | 9/2021 | Schumacher | A61B 17/1615 |

\* cited by examiner

IMPLANT TRIAL WITH RADIOGRAPHICALLY VISIBLE INDICIUM

STATEMENT OF RELATED CASES

This application is a continuation of U.S. Ser. No. 17/308,725, filed May 5, 2021, which claims the benefit of U.S. Provisional Ser. No. 63/020,126, filed May 5, 2024, the entire contents of which are incorporated herein by reference.

FIELD OF THE DISCLOSURE

The present disclosure relates to an implant trial with radiographically visible indicium.

BACKGROUND

Trial spacers can be used to measure the appropriate size of implant needed in orthopedic surgery. It is critical to the success of any surgical procedure and subsequent patient recovery that an appropriately sized device is selected for implantation. However, currently there is no identifier to see the value of depth markers intraoperatively. Depth markers are typically laser marked or inscribed on the top and bottom of the trial spacer but cannot be seen when the trial spacer is in use in vivo. Often, selection of the correct implant size is based on relative position of a reference feature or other fiducial marker, since radiographic techniques are prone to scale or image distortion errors. These defining features may be machined into the boundary of the device to create a visual reference point, but it may be difficult to determine what the particular reference point indicates while used in vivo and typically require an external reference guide to aid in implant selection. Other parameters, other than size of the implant, may also be important.

BRIEF DESCRIPTION OF THE DRAWINGS

Corresponding reference characters indicate corresponding parts throughout the drawings.

DETAILED DESCRIPTION

Figure 1:
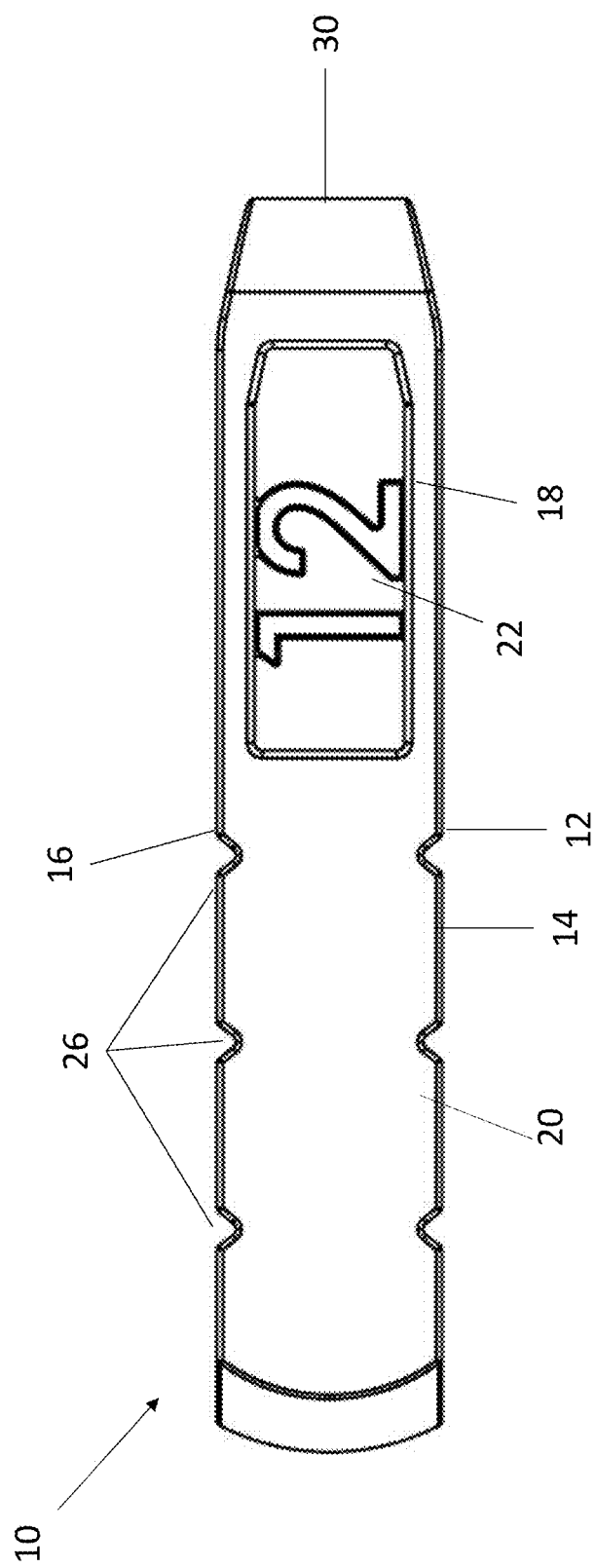
FIG. 1 is a front elevational view of a trial spacer.
Figure 2:
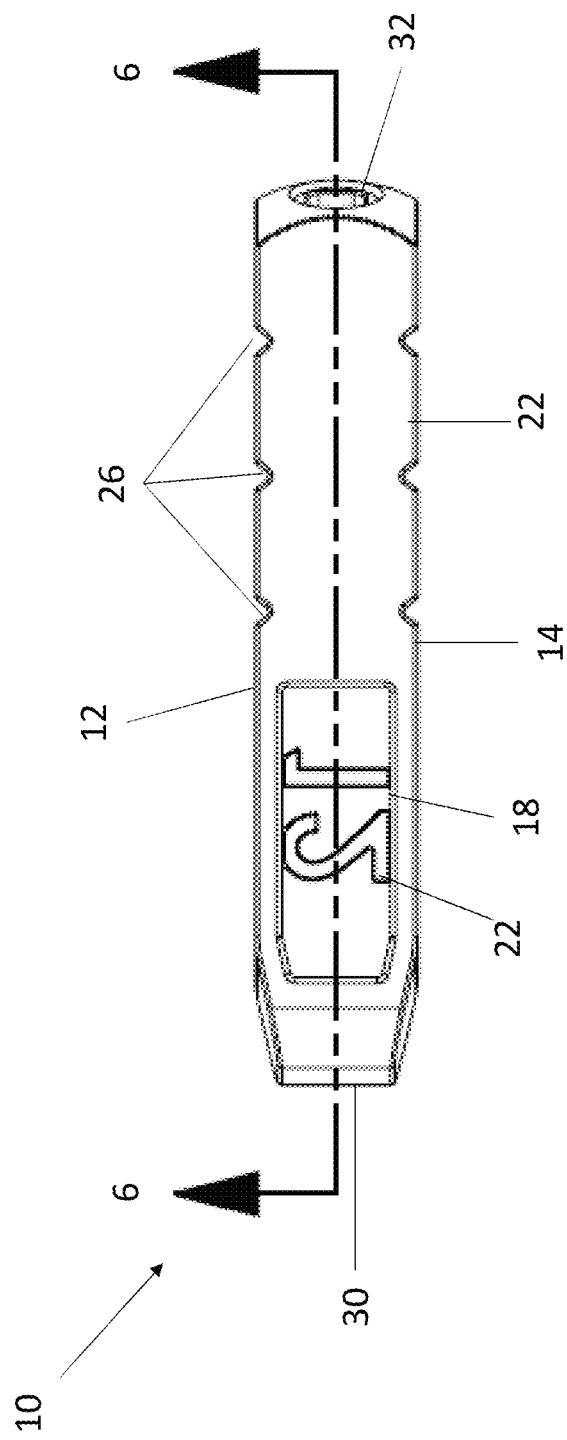
FIG. 2 is a rear elevational view of the trial spacer.
Figure 3:
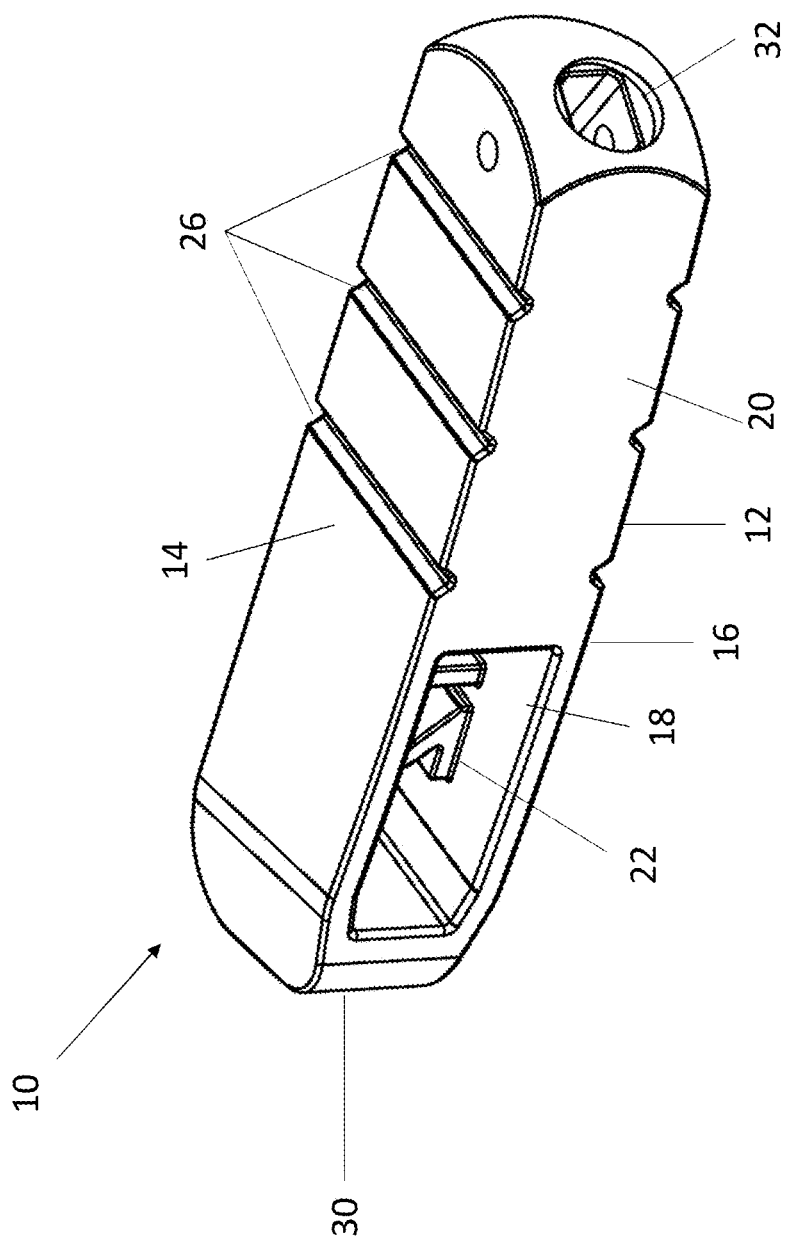
FIG. 3 is a perspective view of the trial spacer.
Figure 4:
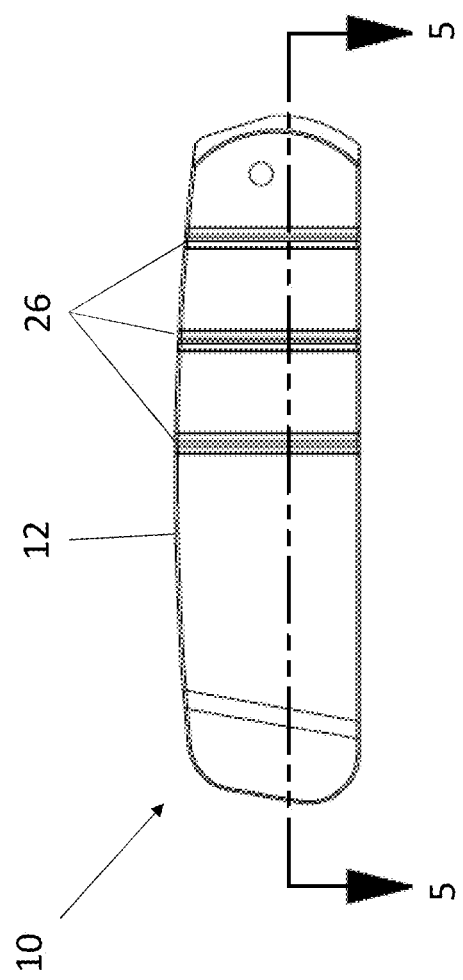
FIG. 4 is a top plan view of the trial spacer.

An implant trial (e.g., spacer trial for spine surgery), constructed according to the teachings of the present disclosure, aids in intraoperative identification of implant size and positioning. The implant trial includes radiographically (e.g., X-ray) visible indicium (e.g., a number, a letter, a logo, or other marking) used for implant sizing and positioning. In one aspect, the implant trial includes a material density gradient to allow one or more X-ray visible indicium to be visible in an X-ray image. The X-ray visible indicium may be provided inside the body of the implant trial, such as within an internal chamber defined by the body. The portion of the implant trial body having the X-ray visible indicium may be sealed from any biological contamination, maintaining optimal surgical function without changing any cleanability or other use criteria. In one example, additive manufacturing may be used to make the X-ray visible indicium and other portions of the implant trial, including the entire implant trial. In another example, materials of two different radiographic density could be molded. However, the skilled person will understand other methods of manufacture are possible. The implant trial can be used in any application where it is desirable to view the implant trial under radiography, such as fluoroscopy, computed tomography (CT scan), and/or projectional radiography. In one embodiment, the implant trial is a trial spacer used in spinal surgery, such as but not limited to lumbar interbody fusions and other spinal fusions procedures.

Referring to FIGS. 1 to 6, the trial spacer (broadly, an implant trial) is generally indicated by reference numeral 10. The trial spacer 10 generally comprises a main body 12 having an inferior wall 14 and a superior wall 16. It will be understood by the skilled person that the terms "superior," "inferior," and other or any other term referencing the relative locations of components and structures of the spacer trial are described in relation to the orientation of the trial spacer as inserted in the body of the patient.

The main body 12 generally comprises a first or distal portion 18 and a second or proximal portion 20. The first portion 18 comprises a visible height marking 22 (e.g., a number). The height marking 22 is indicium and generally indicates the height of the device from the inferior wall 14 to the superior wall 16. The height marking 22 can comprise any signifier of the height of the device, for example, letters, numbers, or any other indicia. The height marking 22 is disposed in a window extending through anterior and posterior sides of the trial spacer 10.

Figure 5:
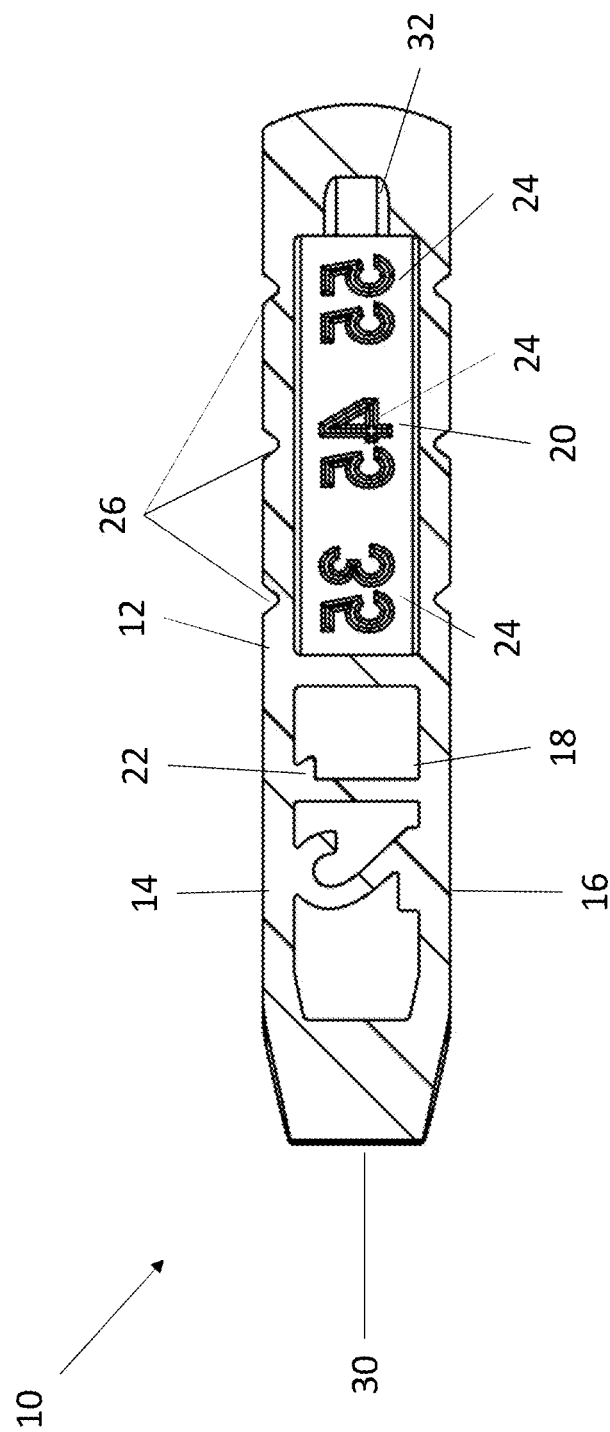
FIG. 5 is a cross section of the trial spacer taken through line 5-5 of FIG. 4.
Figure 6:
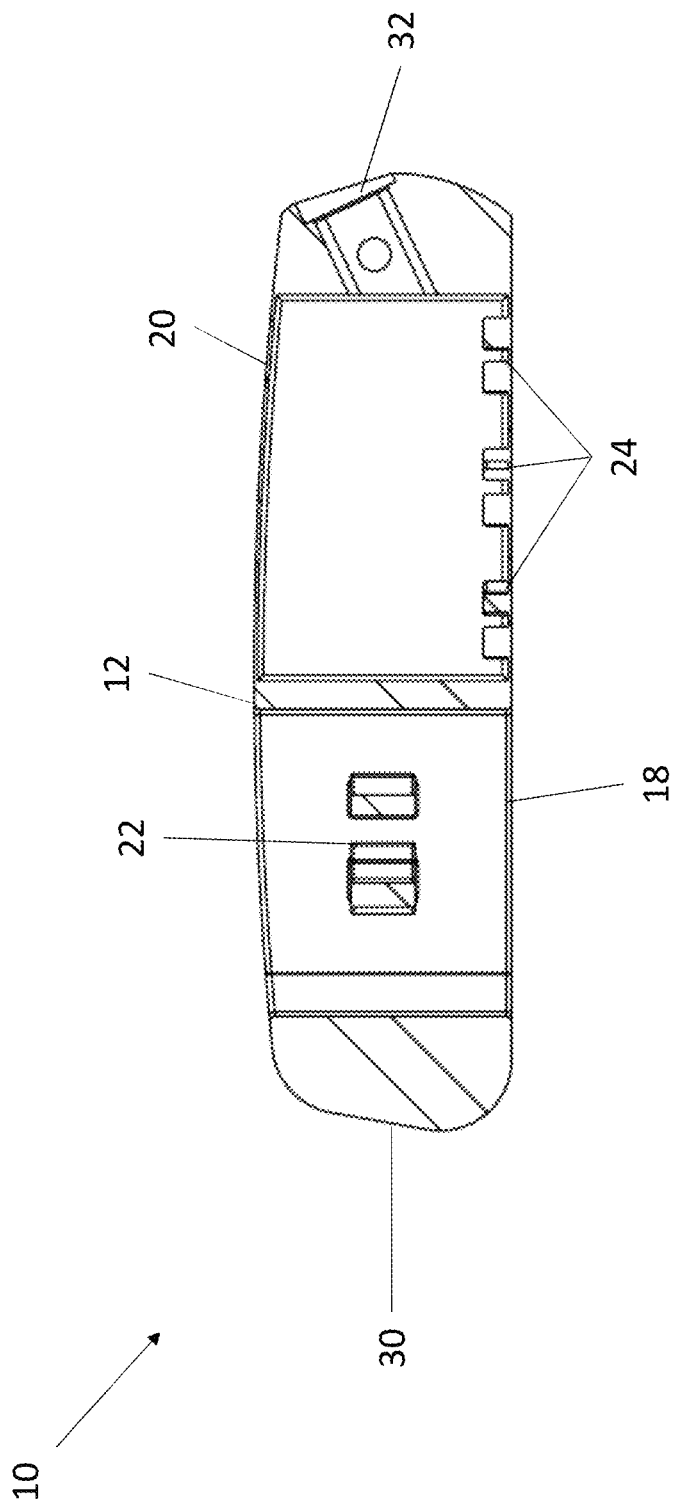
FIG. 6 is a cross section of the trial spacer taken through line 6-6 of FIG. 2.

As shown in FIGS. 5 and 6, the second portion 20 comprises depth indicia 24 (e.g., numbers). The depth indicia 24 are associated with respective depth markers 26 on the exterior of the body 12 (see FIG. 5). In the illustrated embodiment, the depth markers 26 comprise triangle cutouts or notches but can comprise any marking that are visible in radiographic imaging, such as in an X-ray image. The depth indicia 24 generally indicate the length or depth from a nose 30 or distal end of the body 10 to the corresponding depth marker 26. The depth indicia 24 are located within the main body 12 and therefore may not be visible from the outside of trial spacer 10. The depth indicia 24 can comprise any signifier of the length from the nose 30 to the particular depth marker 26, for example, letters, numbers, or any other indicia.

Figure 8:
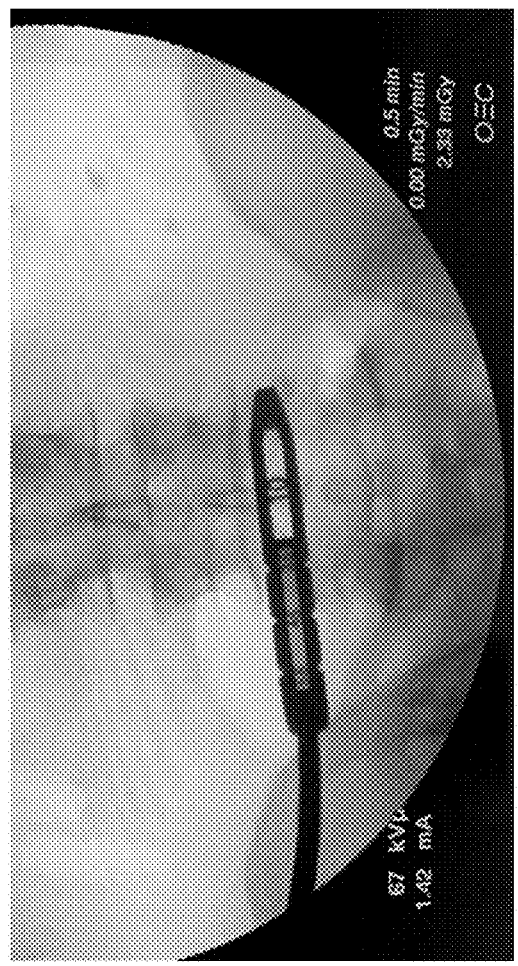
FIG. 8 is an X-ray image of the trial spacer in the vertebral space.

Anterior and posterior walls are provided on the corresponding sides of the second portion 20 of the body 10. Together, the superior wall 16, the inferior wall 14, the anterior wall, and posterior wall define an internal chamber in which the depth indicia 24 are received. The anterior and posterior walls are more radio translucent than the depth indicia 24, which may be substantially radiopaque, so that the depth indicia are visible during radiography, such as shown in FIG. 8. In one example, the anterior and posterior walls are suitably thin to allow X-ray (or other radiation for radiographic imaging) to pass through with little interference, and the depth indicia 24 are made of much thicker material (such as steel) that will absorb the radiation from the X-ray (or other radiographic imaging) and make them visible on the radiographic image itself. The depth indicia 26 may be disposed on or adjacent to the anterior wall, as shown in FIG. 6. The trial spacer 10 can be made by additive manufacturing, such as by using a direct metal laser sintering (DMLS) printer.

The depth indicia are designed to be visible when using X-ray in an anterior-posterior (AP) view (X-ray passing from posterior to anterior). Space is left above, below, and to the sides of the depth indicia 24 to allow them to be visible when viewing the depth indicia 24 from a few degrees from normal to the depth indicia 24.

Alternatively, the depth indicia 24 can be suspended in a material that is more radiolucent than material of the depth indicia. For example, the depth indicia 24 can be printed in steel or any other material that is visible on the desired radiographic imaging radiation (e.g., X-ray) and the remainder of the device can be printed in titanium, aluminum, or any other material through which the particular radiographic imaging radiation can pass more easily so that the depth indicia 24 is more visible than the other material on the image. For example, the depth indicia 24 may be made from material having a greater density than the surrounding material. The skilled person will understand that different methods of manufacture are possible to achieve the same result.

Figure 7:
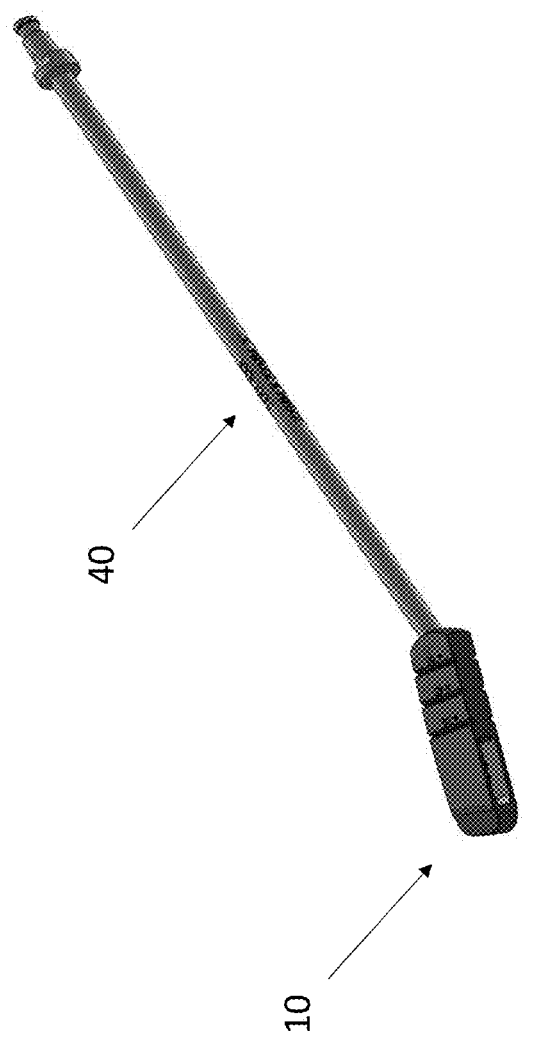
FIG. 7 is a perspective view of the trial spacer in combination with an insertion tool.

The proximal end of the second portion 20 defines opening 32. Opening 32 is sized and shaped to receive an inserter tool 40 to allow for insertion of trial spacer 10 into the vertebral space of the patient (see FIG. 7). As shown in FIG. 6, opening 32 can be disposed at an angle toward the anterior wall in order to provide ease of insertion for the user.

As can be seen in the X-ray image provided in FIG. 8, the height marking is clearly indicated as 10 and the depth indicia are visible whereas the surrounding material is semi-translucent. The user will be able to determine whether the correct height of spacer was chosen based on the height marking and also the depth needed by use of the depth indicia.

The trial spacer of the present disclosure is typically manufactured using 3D printing techniques to create features that may not otherwise be technically manufacturable or are otherwise cost prohibitive. The trial spacer could designed hollow, to further attach to another surgical instrument such as a shaft, or could be produced as one-piece. In the assembled version, during assembly of the trial, a shaft may be welded or threaded in place to completely seal off the internal chamber to prevent the need for the internal chamber to be cleaned between uses.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A trial spacer comprising:
   a spacer body configured to be positioned between vertebrae of a subject, the spacer body having opposite proximal and distal ends, and opposite anterior and posterior sides;
   depth indicia disposed in the spacer body, each of the depth indicia comprising a numerical value indicating a distance proximal from the distal end of the spacer body to a corresponding one of the depth indicia, wherein the depth indicia are radiographically visible when the spacer body is positioned between the vertebrae of the subject; and
   a sizing indicium disposed in the spacer body, the sizing indicium comprising a numerical value to indicate a size of the trial spacer, wherein the sizing indicium is radiographically visible and readable when the spacer body is positioned between the vertebrae of the subject,
   wherein the depth indicia are proximal of the sizing indicium so that the sizing indicium is intermediate the distal end of the spacer body and the depth indicia.

2. The trial spacer set forth in claim 1, wherein the spacer body defines an internal chamber, wherein the depth indicia are is disposed in the internal chamber.

3. The trial spacer set forth in claim 1, wherein each of the depth indicia is designed and constructed to be visible when radiographically viewed in an anterior-posterior view.

4. The trial spacer set forth in claim 3, wherein the sizing indicium is designed and constructed to be visible when radiographically viewed in an anterior-posterior view.

5. The trial spacer set forth in claim 4, wherein the sizing indicium is visible without radiographic imaging.

6. The trial spacer set forth in claim 1, wherein the spacer body defines a window extending through the spacer body, wherein the sizing indicium is visible through the window without radiographic imaging.

7. The trial spacer set forth in claim 1, wherein the depth indicia is enclosed within the spacer body, wherein a portion of the spacer body is more radiolucent than the depth indicia so that the depth indicia is radiographically visible.

8. The trial spacer set forth in claim 1, wherein the spacer body includes a superior wall, an inferior wall, an anterior wall defining the anterior side, and a posterior wall defining the posterior side, wherein the depth indicia is radiographically visible through at least one of the anterior wall and the posterior wall.

9. The trial spacer set forth in claim 1, further comprising depth markers on the spacer body, wherein each depth indicia corresponds to one of the depth markers.

10. A method of making a trial spacer of claim 1, the method comprising forming the spacer body, the depth indicia, and the sizing indicium as an integrally formed, one-piece component by additive manufacturing.

11. A trial spacer comprising:
    a spacer body configured to be positioned between vertebrae of a subject, the spacer body having opposite proximal and distal ends, and opposite anterior and posterior sides;
    a first indicium disclosed within the spacer body and indicating a first parameter of the spacer body, the first indicium comprising a numerical value, wherein the first indicium is radiographically visible in a posterior-anterior direction when the spacer body is positioned between the vertebrae of the subject; and
    a second indicium disposed in the spacer body and indicating a second parameter of the spacer body, the second indicium comprising a numerical value, wherein the second indicium is radiographically visible in a posterior-anterior direction when the spacer body is positioned between the vertebrae of the subject; and wherein the first indicium is proximal of the second indicium so that the second indicium is intermediate the distal end of the spacer body and the first indicium.

12. The trial spacer set forth in claim 11, wherein the second indicium is visible without radiographic imaging.

13. The trial spacer set forth in claim 12, wherein a portion of the spacer body is more radiolucent than the first indicium so that the first indicium is radiographically visible.

14. The trial spacer set forth in claim 13, wherein the spacer body includes a superior wall, and inferior wall, an anterior wall defining the anterior side, and a posterior wall defining the posterior side, wherein the first indicium is radiographically visible through at least one of the anterior wall and the posterior wall.

15. The trial spacer set forth in claim 14, wherein the first indicium is only visible radiographically.

\* \* \* \* \*